(12) United States Patent
Johnston

(10) Patent No.: US 7,298,938 B2
(45) Date of Patent: Nov. 20, 2007

(54) CONFIGURATION MEMORY FOR A SCANNING BEAM DEVICE

(75) Inventor: Richard S. Johnston, Sammamish, WA (US)

(73) Assignee: University of Washington, Seattle, WA (US)

( * ) Notice: Subject to any disclaimer, the term of this patent is extended or adjusted under 35 U.S.C. 154(b) by 184 days.

(21) Appl. No.: 10/956,473

(22) Filed: Oct. 1, 2004

(65) Prior Publication Data

US 2006/0072874 A1 Apr. 6, 2006

(51) Int. Cl.
G02B 6/26 (2006.01)
(52) U.S. Cl. .............................. 385/25; 385/15; 385/53
(58) Field of Classification Search ................. 385/15, 385/25, 53
See application file for complete search history.

(56) References Cited

U.S. PATENT DOCUMENTS

| | | | |
|---|---|---|---|
| 4,527,893 A | 7/1985 | Taylor | |
| 4,677,683 A * | 6/1987 | Pferd et al. | 382/141 |
| 4,767,911 A | 8/1988 | Maram | |
| 4,919,508 A | 4/1990 | Grace et al. | |
| 4,972,344 A | 11/1990 | Stoddard | |
| 4,991,971 A | 2/1991 | Geary et al. | |
| 5,011,259 A | 4/1991 | Lieber et al. | |
| 5,172,685 A | 12/1992 | Nudelman | |
| 5,317,148 A | 5/1994 | Gray et al. | |
| 5,400,267 A | 3/1995 | Denen et al. | |
| 5,625,451 A | 4/1997 | Schiff et al. | |
| 5,681,307 A | 10/1997 | McMahan | |
| 5,693,042 A | 12/1997 | Boiarski et al. | |
| 5,727,098 A | 3/1998 | Jacobson | |
| 5,742,718 A | 4/1998 | Harman et al. | |
| 5,764,874 A | 6/1998 | White | |
| 5,768,461 A | 6/1998 | Svetkoff et al. | |
| 5,822,486 A | 10/1998 | Svetkoff et al. | |
| 5,870,511 A | 2/1999 | Sawatari et al. | |
| 5,907,425 A | 5/1999 | Dickensheets et al. | |
| 5,933,240 A | 8/1999 | Jurca | |
| 6,046,720 A | 4/2000 | Melville et al. | |
| 6,091,067 A | 7/2000 | Drobot et al. | |

(Continued)

FOREIGN PATENT DOCUMENTS

WO WO 00/75712 12/2000

OTHER PUBLICATIONS

"Engineering Study of an Endoscope Design," *Human Interface Technology*, <www.hitl.washington.edu/research/endoscope/> (Sep. 30, 2004).

(Continued)

*Primary Examiner*—Jennifer Doan
(74) *Attorney, Agent, or Firm*—Townsend and Townsend and Crew LLP

(57) ABSTRACT

The present invention provides a memory element for providing compatibility information and/or parametric data about a scanning beam device to a universal base station. The present invention provides a memory coupled to the scanning beam device that provides parametric data, such as an identifier code, compatibility information, and other characteristics of the scanning beam device that is coupled to the universal base station. A controller of the base station may use the parametric data to configure or generate a control routine so as to allow the base station to properly operate the device.

48 Claims, 5 Drawing Sheets

U.S. PATENT DOCUMENTS

| | | | |
|---|---|---|---|
| 6,211,904 B1 | 4/2001 | Adair et al. | |
| 6,222,628 B1 | 4/2001 | Corallo et al. | |
| 6,294,775 B1 | 9/2001 | Seibel et al. | |
| 6,327,493 B1 | 12/2001 | Ozawa et al. | |
| 6,329,778 B1 | 12/2001 | Culp et al. | |
| 6,388,641 B2 | 5/2002 | Tidwell et al. | |
| 6,402,743 B1 | 6/2002 | Orszulak et al. | |
| 6,411,838 B1 | 6/2002 | Nordstrom et al. | |
| 6,492,962 B2 | 12/2002 | Melville et al. | |
| 6,498,948 B1 | 12/2002 | Ozawa et al. | |
| 6,563,105 B2 | 5/2003 | Seibel et al. | |
| 6,564,087 B1 | 5/2003 | Pitris et al. | |
| 6,626,834 B2 | 9/2003 | Dunne | |
| 6,627,903 B1 | 9/2003 | Hirayanagi | |
| 6,666,860 B1 | 12/2003 | Takahashi | |
| 6,747,753 B1 * | 6/2004 | Yamamoto | 358/1.15 |
| 6,845,190 B1 | 1/2005 | Smithwick et al. | |
| 2001/0030744 A1 | 10/2001 | Chang | |
| 2001/0055462 A1 | 12/2001 | Seibel | |
| 2002/0064341 A1 | 5/2002 | Fauver et al. | |
| 2002/0131052 A1 | 9/2002 | Emery | |
| 2003/0010826 A1 | 1/2003 | Dvorkis et al. | |
| 2003/0086161 A1 | 5/2003 | Harris | |
| 2003/0179428 A1 | 9/2003 | Suzuki et al. | |
| 2004/0076319 A1 | 4/2004 | Fauver et al. | |
| 2004/0113059 A1 | 6/2004 | Kawano et al. | |
| 2004/0254474 A1 | 12/2004 | Seibel et al. | |
| 2006/0072843 A1 | 4/2006 | Johnston et al. | |
| 2006/0138238 A1 | 6/2006 | Johnston et al. | |
| 2006/0186325 A1 | 8/2006 | Johnston et al. | |

OTHER PUBLICATIONS

"Micro-Optical Fabrication of a Fiber Scanning System," *Human Inerfact Technology*, <www.hitl.washington.edu/projects/mfabfiber/> (Sep. 29, 2004).

"Q factor" from *Wikipedia, The Free Encyclopedia*, May 20, 2004, <www.en.wikipedia.org/wiki/Q_factor> (Jun. 22, 2004).

Brown, C. et al., "A Novel Design for a Scanning Fiberoptic Endoscope".

Brown, C. et al., "Mechanical Design and Analysis for a Scanning Fiber Endoscope," *ASME*, BED-vol. 50, pp. 1-2, (2001).

Fauver, M. et al., "Microfabrication of Fiber Optic Scanners," *Proc. of Optical Scanning II, SPIE*, 4773:102-110 (2002).

Johnson, Brent, "Grating Shrinks Endoscope," *Photonics Spectra*, (Oct. 2003), <www.photonics.com/spectra/applications/QX/ASP/aoaid.335/QX/read.htm> (Sep. 30, 2004).

Piyawattanametha, W. et al., "A MEMS Non-Interferometric Differential Confocal Scanning Optical Microscope" (2000).

Seibel, E. and Smithwick, Q., "Unique Features of Scanning Fiber Optical Endoscopy," *Annals of Biomedical Engineering*, 28 (suppl. 1), S-40 (2000).

Seibel, E. et al., "Prototype Scanning Fiber Endoscope," presented at *SPIE BiOS*, San Jose, CA (Jan. 2002).

Seibel, E. et al., "Single Fiber Flexible Endoscope: General Design for Small Size, High Resolution, and Wide Field of View," *Proc. of the SPIE, Biomonitoring and Endoscopy Technologies*, 4158:pp. 29-39 (2001).

Seven, Richard, "At the UW Hit Lab, There's Virtue in Virtual Reality," Seattletimes.com, Apr. 11, 2004, <www.seattletimes.nwsource.com/pacificnw/2004/0411/cover.html> (Jun. 9, 2004).

Smithwick, Q. et al., "Control Aspects of the Single Fiber Scanning Endoscope," *SPIE Optical Fibers and Sensors for Medical Applications*, 4253:176-188 (2001).

Smithwick, Q. et al., "Depth Enhancement Using a Scanning Fiber Optical Endoscope," presented at *SPIE BiOS*, San Jose, CA (Jan. 2002).

Smithwick, Q. et al., "Modeling and Control of a Resonant Fiber Scanner for Laser Scanning Display or Acquisition," Technical Report, Department of Aeronautics and Astronautics and Human Interface Technology Laboratory, University of Washington (May 22, 2003).

Smithwick, Q. et al., "Modeling and Control of the Resonant Fiber Scanner for Laser Scanning Display or Acquisition," *SID 03 Digest*, pp. 1455-1457 (2003).

Tearney, G. et al., "Scanning Single-Mode Fiber Optic Catheter-Endoscope for Optical Coherence Tomography," *Optics Letters*, 21(7):543-545 (Apr. 1, 1996).

Wang, W. et al., "Development of an Optical Waveguide Cantilever Scanner," *Proc. of SPIE*, 4876:72-83 (2002).

Wang, W. et al., "Micromachined Optical Waveguide Cantilever as a Resonant Optical Scanner," *Sensors and Actuators A*, 102:165-175 (2002).

Andersen, J. and Seibel, E., "Real-Time Hazard Detection Via Machine Vision for Wearable Low Vision Aids," *5th Intl. Symposium on Wearable Computers, Proceedings of IEEE ISWC* 2001, pp. 182-183.

Johnston, R. et al., U.S. Appl. No. 11/094,017, filed Mar. 29, 2005.

\* cited by examiner

CONFIGURATION MEMORY FOR A SCANNING BEAM DEVICE

BACKGROUND OF THE INVENTION

The present invention relates generally to scanning beam devices. More specifically, the present invention relates to scanning fiber devices that have a memory element which includes data that improves operation of the scanning fiber devices.

There is a growing market for micro-optical displays and small image acquisition systems (e.g., cameras). Scanning beam systems fill the need, but the lack of low cost micro-optical systems with a wide field of view (FOV) have been the most significant barrier for reducing the size of scanning beam systems for use in minimally invasive medical imaging (flexible endoscopes), surveillance, industrial inspection and repair, machine and robotic vision systems, and micro-barcode scanners.

Most conventional scanning beam systems use a movable scanning element, such as a rotating or oscillating mirror. Light, such as a laser beam, is projected onto the moving mirror to scan the light across a predetermined linear pattern or two-dimensional pattern (e.g., raster) at a scan frequency that is sufficient for the particular application. The FOV is determined by the scanning amplitude and the particular optical design of the system. While the scanning element may be scanned at any frequency, in most embodiments, a drive signal is chosen to substantially match the resonant frequency of the scanning element. As shown in FIG. 1A, it is often useful to scan the light at a frequency within a "Q-factor" of the resonant frequency of the scanning element. Scanning the light within the Q-factor allows for scanning at desired angles and displacements while using a minimal amount of energy to obtain the desired angles and displacement.

Combining both high resolution (>400,000 pixels) and wide FOV (>30 degrees) in a single display or camera is a difficult technical challenge. There is a tradeoff between optical scanning frequency versus scanning amplitude (FOV) for all mirror-scanning devices. The faster the mirror scans, the greater the forces acting on the mirror, which deforms the mirror surface, degrading image quality. This limitation is especially true for the small, low cost resonant mirror scanners. Rotating polygon mirror scanners can overcome this limitation or tradeoff between scan frequency and amplitude, except they are usually bulky, and costly. In the case of a resonant mirror scanner, the mirror cannot scan more than a few degrees in amplitude at frequencies of 20 kHz to 40 kHz, as required for sVGA raster scanning displays. Since the optical beam reflects from the scanning mirror, the optical FOV is twice the total mirror deflection angle (i.e., the FOV=2 times mirror scan amplitude). However, at sVGA resolution and scan frequencies, optical FOVs on the order of 30 degrees to 60 degrees cannot be achieved using a low cost resonant mirror scanner as the basis for micro displays.

Recently, resonant mirror optical scanning systems have been developed that include silicon micro-machining techniques to make micro-electromechanical systems (or MEMS) devices. In theory, this technique can manufacture durable mirror-based optical scanners at lower costs. Nonetheless, there is still a tradeoff between scan amplitude and scan frequency of the resonant scanning mirror.

To that end, an improved scanning beam system has been developed which involves the use of a cantilevered optical fiber that is scanned in one or two dimensions to project light out of the end of the optical fiber to form an image. In addition to image formation and micro-display applications, image acquisition is also possible with the addition of a sensor, such as a photosensor. To acquire an image, the light projected out the end of the scanning optical fiber is reflected from the target area and the backscattered light is captured and measured with the sensor in time series. Because the motion of the fiber is predictable and repeatable, the reflected light intensity measured at the sensor can be sequentially correlated with the position of the optical fiber, and a two-dimensional image may be created one 'pixel' at a time. For ease of reference, the terms "scanning beam system" and "scanning fiber system" will be used generically to encompass systems that are used for image display and/or image acquisition.

In comparison to traditional scanning beam devices, scanning fiber technology offers many advantages. The small mass of the optical fiber scanner allows high scan angles at video rates—typically between about 1 kHz and about 50 kHz, and preferably between about 5 kHz and about 25 kHz. Optical fiber scanners also have a smaller 'footprint', taking up less space and can be conveniently packaged into a small (<1 mm) diameter cylindrical endoscope or catheter housing.

When used for image acquisition, the fiber scanner has numerous applications in the areas of medical endoscopy and other remote imaging methods, where the millimeter package diameter size allows exploration into areas previously untouched by traditional methods. Commonly owned U.S. Pat. Nos. 6,563,105 B2 and 6,294,775 B1 and U.S. Patent Application Publication Nos. 2001/0055462 A1, and 2002/0064341 A1 (all to Seibel) describe some useful image acquisition systems, the complete disclosures of which are incorporated herein by reference.

It is contemplated that commercial scanning beam systems of the present invention will comprise a base station and a scanning beam device. One particular use of the systems of the present invention is for minimally invasive medical procedures in which the scanning beam device is in the form of a flexible endoscope that may be used to image an interior of a body lumen, body cavity, and/or hollow organ. As can be appreciated, for different body lumens or for different imaging procedures, it may be desirable to use different devices that have different properties, such as different sizes, fields-of-view, resolutions, color capability, or the like. However, the differences in characteristics for each of the devices will generally require a different control routine to properly operate the device and to be able to take advantage of the capabilities of the device. In particular, the devices will often have different resonant frequencies, and the base station will need to alter a drive signal to match the resonant frequency of the specific fiber.

Importantly, even if two of the same model scanning beam devices are used with the base station, because of manufacturing tolerances, oftentimes the two same model devices will still have differences in their resonant frequencies or other parameters that will affect the operation of the device. Consequently, in order to be able to use a single base station with the different scanning beam devices, it may be necessary to determine the operating parameters for each and every device prior to use so that the base station can reconfigure its control routine to match the parameters of the device. Without such parametric data, the base station may not be able to properly operate the different of scanning beam devices. While it is may be possible to determine the parameters of each device, such calibration is time consuming and lengthens the setup procedure. In some cases, it may not even be possible to determine all of the relevant parameters of the device. As different models of devices are developed for use with the base stations, in which each of the devices will have different characteristics than other models, the time involved in reconfiguring the base station to allow the base station to take advantage of the different capabilities of the devices will increase and will add significantly to the time of the scanning procedure.

In light of the above, it would be desirable to provide improved base stations, devices, systems, and methods. It would be further desirable to provide universal base stations that have a reduced set up time and reduced number of calculations associated with reconfiguring a base station for use with different devices. It would be especially desirable if the enhanced and rapid configuration methods resulted in improved safety to the patient and reliability of image construction.

BRIEF SUMMARY OF THE INVENTION

The present invention relates generally to scanning beam systems and scanning beam devices which incorporate a memory structure (such as a non-volatile memory) for providing parametric data of the scanning beam device to a controller of a base station. The memory may provide an identification of the device and/or parametric data that allows the controller to configure a control routine (e.g., scan pattern) to match the parametric data of the attached device, change the display properties of the base station, change the operator controls on the base station, change the use profile, or the like. The data from the memory will allow the base station to properly operate the device and take advantage of the capabilities of the device.

The memory is typically a non-volatile memory such as FLASH memory, EEPROM, non-volatile RAM, Flash EPROM, battery backed up SRAM, EPROM, PROM, ROM, and the like. The memory may be mounted on a connector member that interfaces with the base station, on or in a housing of the device, or any other place on the device.

Scanning beam systems of the present invention may be usable for image acquisition and/or image display. The systems of the present invention includes a base station and one or more scanning beam devices. If the scanning beam devices are used for image acquisition, the devices may comprise at least one detector for capturing backscattered light from a target area.

The devices include a waveguide, such as an optical fiber that conveys electromagnetic energy such as light between its opposite ends. In most of the discussion set forth below, an optical fiber is a preferred kind of waveguide, but it is not intended that the present invention be in any way limited to an optical fiber or limited to only conveying visible light. In one embodiment, the device directs light out of the distal end of an optical fiber to form an illumination spot on the target area. A piezoelectric or other electro-mechanical assembly is driven by a drive signal to scan the optical fiber so that the illumination spot is scanned over the target area in a desired scan pattern. Light reflected from the target area is collected by the detector and the light or a light signal is routed to the base station. Since the position of the illumination spot is precisely controlled during the scan pattern by the drive signal, the controller is substantially able to synchronize the captured light (e.g., illumination spot) with a specific time point in the scan pattern. Using the known scan pattern and timing of the scan pattern, the controller of the base station is then able to time place the captured light to a specific portion or "pixel" of the reconstructed image. By knowing the position of the illumination spot on the target area for every instant in time of the scan pattern, the image may be constructed one pixel at a time.

While the optical fiber may be scanned at any frequency, in most embodiments, a drive signal is typically within a Q-factor of the resonant frequency, and preferably at the resonant frequency of the optical fiber. Scanning at the resonant frequency provides the desired radial displacement of the optical fiber with a minimal amount of energy. As can be appreciated, other scan frequencies outside the Q-factor may also be used, but a larger amount of energy will be needed to achieve the desired radial displacement of the optical fiber.

In one aspect, the present invention provides a method of operating a scanning beam device. The method comprises providing a scanning beam device that comprises a memory in communication with a connector member. The connector member is coupled to an interface on a base station so as to create a data path between the memory and a controller of the base station. Data is read from the memory of the scanning fiber device. A control routine is generated for operating the scanning beam device and the base station, based at least in part on the data read from the memory. The scanning beam device is then controlled with the control routine that was generated based on the data from the memory.

In one configuration, the data in the memory comprises compatibility data, such as a unique identifier. The unique identifier may be a unique serial number, a model number, or the like. Parametric data that is associated with the unique identifier may stored in the memory of the base station or the memory of the scanning beam device. The parametric data may be used to generate the control routine for the device.

The parametric data my include a resonant frequency of the device. The resonant frequency data will be used by the controller to generate the control routine that corresponds to the resonant frequency. In other embodiments, the parametric data includes a resonant frequency range. The resonant frequency range will provide a limited search range for the controller to search for the resonant frequency of the optical fiber. The controller may scan through the resonant frequency range to determine the resonant frequency for the fiber, and the scanning fiber device may thereafter be scanned substantially at the resonant frequency.

Applicants have found that the resonant frequency of the device may change with the environmental conditions. Therefore, the memory may optionally store different parametric data sets (e.g., remapping tables, resonant frequency, and/or resonant frequency ranges, etc.) that correspond to different environmental conditions (e.g., temperature). In such embodiments, the base station or the scanning beam device may have a sensor (e.g., temperature sensor) to measure the environmental conditions, or a user may be prompted to enter the relevant environmental condition information during a setup procedure. Depending on the measured/entered environmental condition, the base station will be configured to use the appropriate parametric data set on the memory to control the scanning beam device.

The parametric data may also include, but is not limited to, a maximum drive voltage for the drive assembly of the scanned beam device, an expiration data or date of manufacture, zoom or focus capability of the scanning beam device, image remapping algorithms or look up tables, color capability, sensor configuration, or the like.

In another aspect, the present invention provides a scanning beam device comprising a drive assembly coupled to the scanning element. The device comprises a memory with data. A connector member is in communication with the memory, the connector member releasably couples the scanning fiber device to an interface in a base station, wherein coupling of the connector member to the interface in the base station creates a data path from the memory to a controller of the base station. Operation of the scanning fiber device is carried out with a control routine that is based at least in part on data transmitted from the memory to the controller.

In one exemplary embodiment, the scanning element is an optical fiber comprising a proximal end and a distal end, and the drive assembly is configured to scan a distal end of the optical fiber in a desired scan pattern. The data transmitted from the memory typically includes at least one of a compatibility data and identification data (such as a serial number, model number, or the like) The identification data may be associated with a look up table in a database. The look up table may comprise the relevant parametric data of the device. The parametric data may then be used by the controller to generate a control routine that allows for proper operation of the device.

The parametric data may include a resonant frequency data, a resonant frequency range, drive assembly characteristics (such as maximum voltage, etc.), fiber characteristics (diameter, fiber bending and position control data, etc.), expiration dates, data of manufacture, image correction data (correction algorithms or look up tables), detection assembly characteristics (color capability, stereo capability, etc.), or the like.

In another aspect, the present invention provides a base station that is configured to operate a plurality of different scanning fiber devices, the base station comprises a housing that has an interface that is configured to releasably receive a connector member of a scanning fiber device. A controller is in communication with the interface and is configured to be electrically coupled to the scanning fiber device through the interface. The base station comprises a memory that is in communication with the controller. The memory is configured to store a plurality of code modules which when executed by the controller causes the controller to read data from a memory of the scanning fiber device and generate a control routine for a drive assembly of the scanning fiber device to scan the fiber scanning device at a desired scan frequency. The control routine is generated at least in part on the data read from the memory of the scanning fiber device.

The base station will typically include one or more types of power sources that are under the control of the controller. The controller and power source will send a drive signal to the drive assembly to scan the device. The power source may also be used to transmit power through the interface to the memory of the scanning fiber device. The power transmitted through the connector member and memory of the scanning fiber device creates a data path between the controller of the base station and the memory of the scanning fiber device.

The base station may further include one or more illumination sources. The illumination source is configured to transmit light to the scanning fiber device through the interface. The light sources may include a laser source, a visible light source, a UV source, a RGB source, and/or an IR source.

In another aspect, the present invention provides a scanning beam system that comprises a base station comprising a memory coupled to a controller and a light source. The system also includes at least one scanning beam device, such as a scanning fiber device. Each scanning fiber device comprises a scanning fiber comprising a proximal end and a distal end, a drive assembly coupled to the fiber to control scanning of the distal end of the scanning fiber, a connector member for coupling the scanning fiber device to an interface in the base station and a memory in communication with the connector member. Coupling of the connector member from one of the fiber scanning devices into the interface in the base station creates a data path from the memory of the scanning fiber device to a controller of the base station and an optical path between the light source to the scanning fiber. The controller of the base station is configured to read data from the memory of the scanning fiber device and initiate a control routine to drive the drive assembly of the scanning fiber device so as to scan the fiber scanning device at a desired scan frequency, wherein the control routine is generated at least in part on the data read from the memory of the scanning fiber.

Other aspects, objects and advantages of the invention will be apparent from the detailed description that follows.

DETAILED DESCRIPTION OF THE INVENTION

The scanning beam systems of the present invention will generally include a scanning beam device and a base station for controlling the scanning beam device. The scanning beam devices of the present invention may take on a variety of forms, but are typically in the form of a rigid or flexible endoscope, catheter, fiberscope, microscope, boroscope, bar code reader, an image display, or other device for generating images or acquiring images of a target area. The scanning beam devices of the present invention may be a limited use device (e.g., disposable device) or a multiple-use device. If the device is for medical use, the scanning beam devices will generally be sterile, either being sterilizable or being provided in hermetically sealed package for use.

The scanning beam devices of the present invention include a scanning element for scanning a beam of light onto a target area. The scanning element preferably comprises a single, cantilevered optical fiber, but in other embodiments, the scanning element may take the form of a mirror, such as microelectomechanical system (MEMS), a galvanometer, a polygon, multiple optical elements moved relative to each other, or the like. While the remaining discussion focuses on a flexible, scanning fiber endoscope that is used for acquiring images of a target site within a body, it will be appreciated that the present invention also encompasses the other aforementioned devices.

Figure 1:
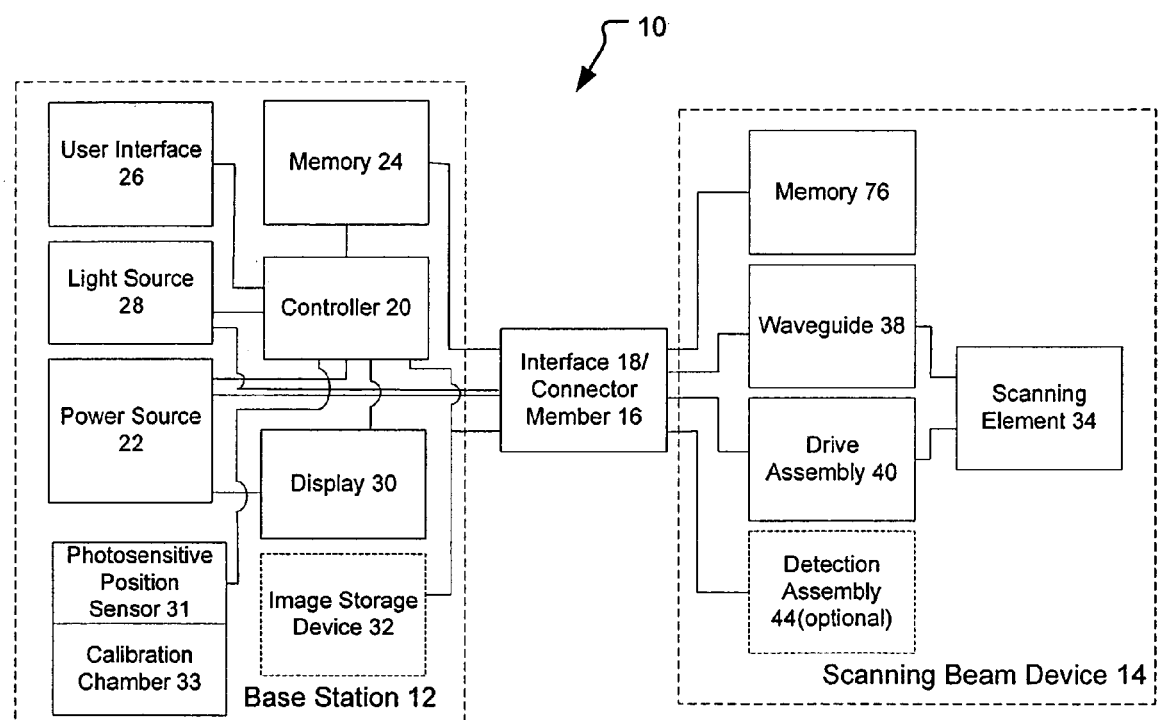
FIG. 1 schematically illustrates a fiber scanning system encompassed by the present invention.

FIG. 1 schematically illustrates a scanning beam system 10 encompassed by the present invention. The scanning beam system 10 includes a base station 12 and a scanning beam device 14. The scanning beam device 14 includes a connector member 16 that is configured to mate with an input interface 18 on the base station. Coupling of the connector member 16 to the input interface 18 may create a power path, drive path, detector path, illumination path, and/or data communication path between elements of the base station 12 and corresponding elements of the scanning beam device 14. The input interface 18 on the base station 12 may be configured to receive and operate a plurality of different compatible scanning beam devices 14 that have different characteristics. Being able to utilize different models of the scanning beam device provides the operator with ability to use a device that best meets the needs of the particular procedure—whether it be image acquisition or image display.

Base station 12 of the present invention typically includes a controller 20 that has one or more microprocessors and/or one or more dedicated electronics circuits which may include a gate array (not shown) which may control the actuation of the scanning beam device 14 and generation of the images. The controller 20 may also include scanner drive electronics, detector amplifiers and A/D converters (not shown). The processor in controller 20 may receive instructions from software modules that are stored in a memory 24. As will be appreciated by those of skill in the art, the methods of the present invention may be carried out by the software modules and/or by the electronics hardware in the controller.

Controller 20 is in communication with a plurality of elements within the base station 12 via a communication bus (not shown). In the simplified configuration of FIG. 1, the communication bus allows for electrical communication between controller 20, a power source 22, memory 24, user interface(s) 26, a light source 28, one or more displays 30, a photosensitive position sensor 31 in a calibration chamber 33. Optionally, if the scanning beam device 14 includes a detection assembly, the base station 12 may include a separate image storage device 32. In alternative embodiments, the image storage device 32 may simply be a module within memory 24. As can be appreciated, the base stations 12 of the present invention will vary, and may include fewer or more modules. For ease of reference, other conventional elements of the base station, e.g., amplifiers, D/A converters, A/D converters, and the like, are not illustrated, but those of skill in the art will recognize that the controllers of the present invention may include such elements.

Light source 28 is configured to emit a continuous stream of light, modulated light, or a stream of light pulses. Base station 12 may comprise a plurality of different light sources 28 so as to be able to operate different scanning beam devices that have different illumination capabilities. The light sources 28 may include one or more of a red light source, blue light source, green light source (collectively referred to herein as a "RGB light source"), an IR light source, a UV light source, and/or a high intensity laser source (typically for a therapeutic scanning beam device). The light sources 28 themselves may be configured to be switchable between a first mode (e.g., continuous stream) and a second mode (e.g., stream of light pulses). The light source 28 enabled by controller 20 will depend on the capabilities of the attached scanning beam device 14 and the control routine stored in memory 24 or 76. For ease of reference, other conventional elements in the light source are not shown. For example, if a RGB light source is used, the light sources may include combiner to combine the different frequency light before the light enters a waveguide 38.

Memory 24 is used for storing the software modules and algorithms for operating the base station and the various scanning fiber devices 14 that are compatible with the base station 12. The software used by the controller 20 for controlling the scanning beam device 14 will typically be configurable so as to match the operating parameters of the attached device (e.g., resonant frequency, voltage limits, zoom capability, color capability, etc.). As noted above, memory 24 may also be use for storing the image data received from the detectors 44 of the scanning beam device.

User interface 26 will include the operator controls for the base station and the scanning beam device 14. User interface 26 may include a keyboard, buttons, switches, joysticks, a mouse, a touchscreen, and the like. The user interface 26 may be configurable by the controller 20 so as to conform to the capabilities of the scanning beam device coupled to the base station 12.

Figure 1A:
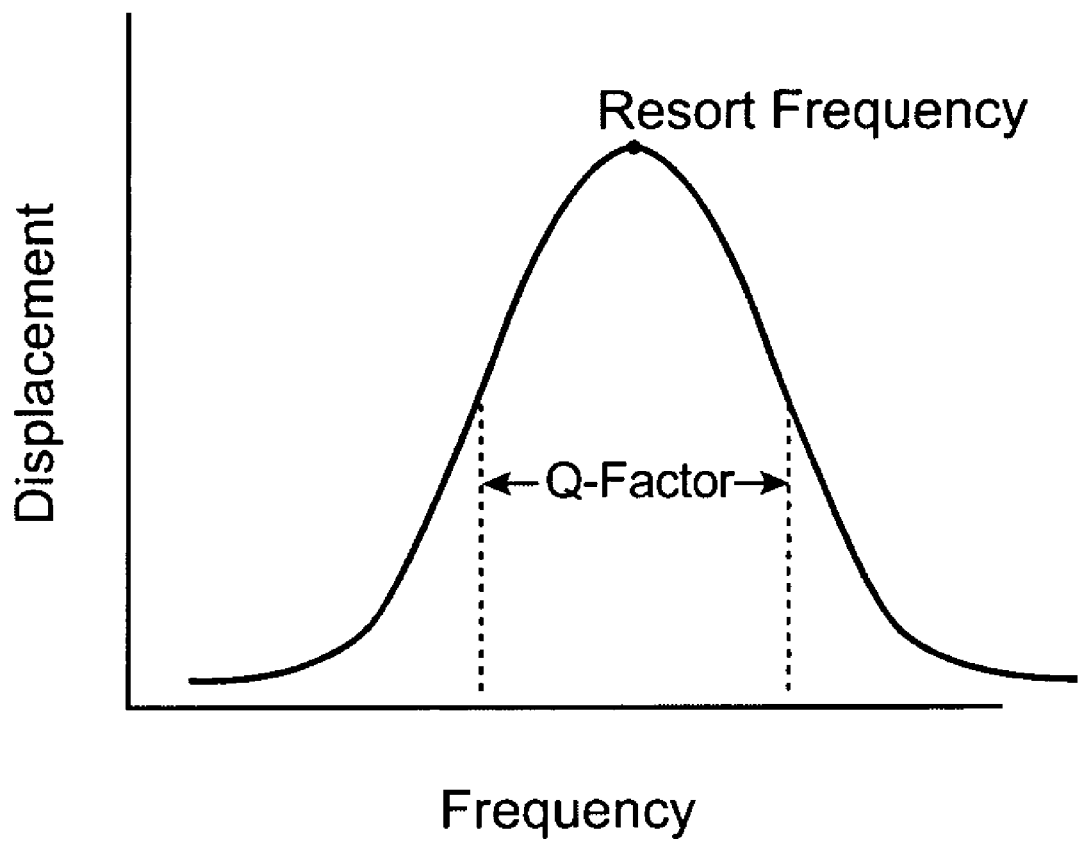
FIG. 1A illustrates a resonant frequency of an optical fiber and a Q-factor.

The scanning beam devices 14 of the present invention typically include a scanning element 34 for scanning a beam of light onto a target area 36. A waveguide 38 delivers illumination from the light source 28 to the scanning element 34. A driving assembly 40 is coupled to the scanning element 34 and is adapted to scan the scanning element 34 according to a drive signal received from the controller 20. Drive assembly 40 will typically drive the scanning element 34 at or near its resonant frequency in one or two dimensions (e.g., typically within a Q-factor of the resonant frequency, see FIG. 1A). As can be appreciated, the scanning element 34 does not have to be driven at substantially the resonant frequency, but if the scanning element is not scanned at its resonant frequency, a larger amount of energy is needed to provide the desired angular displacement for the scan.

Figure 2:
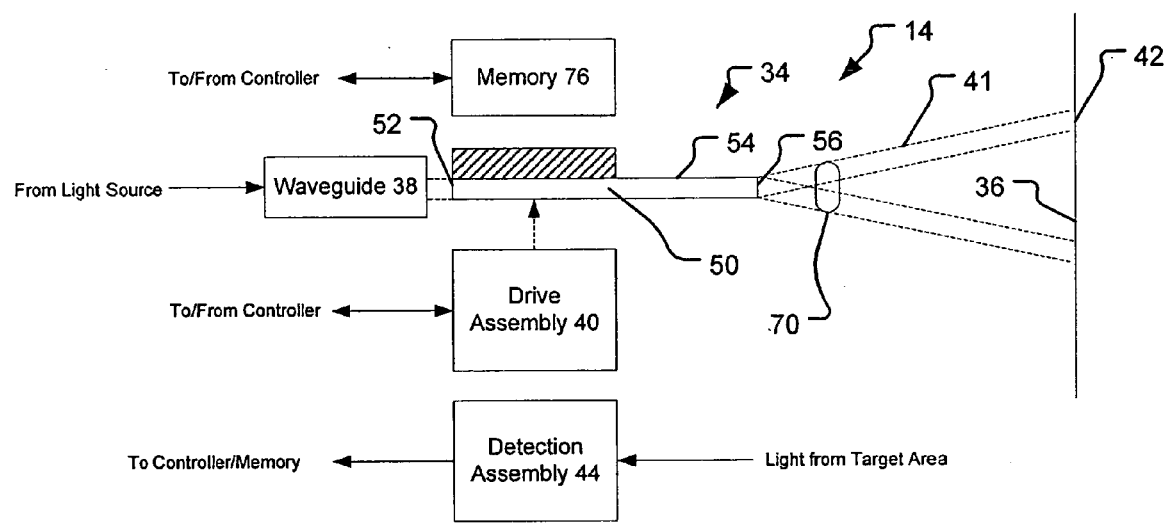
FIG. 2 schematically illustrates a scanning beam device that comprises a scanning element in the form of an optical fiber that is scanned in a scan pattern with an driving assembly.

As shown in FIG. 2, when driven by the drive assembly 40, scanning element 34 scans a beam of illumination 41 and forms a spot on the target area 36 (the "spot" is referred to herein as an "illumination spot 42"). The scanned illumination spot 42 may be used to create an image on the target area 36, or the light reflected off of the target area 36 from the scanned illumination spot 42 may be captured by a detection assembly 44, and the collected light may be used to generate a real-time image of the target area 36.

Figure 3:
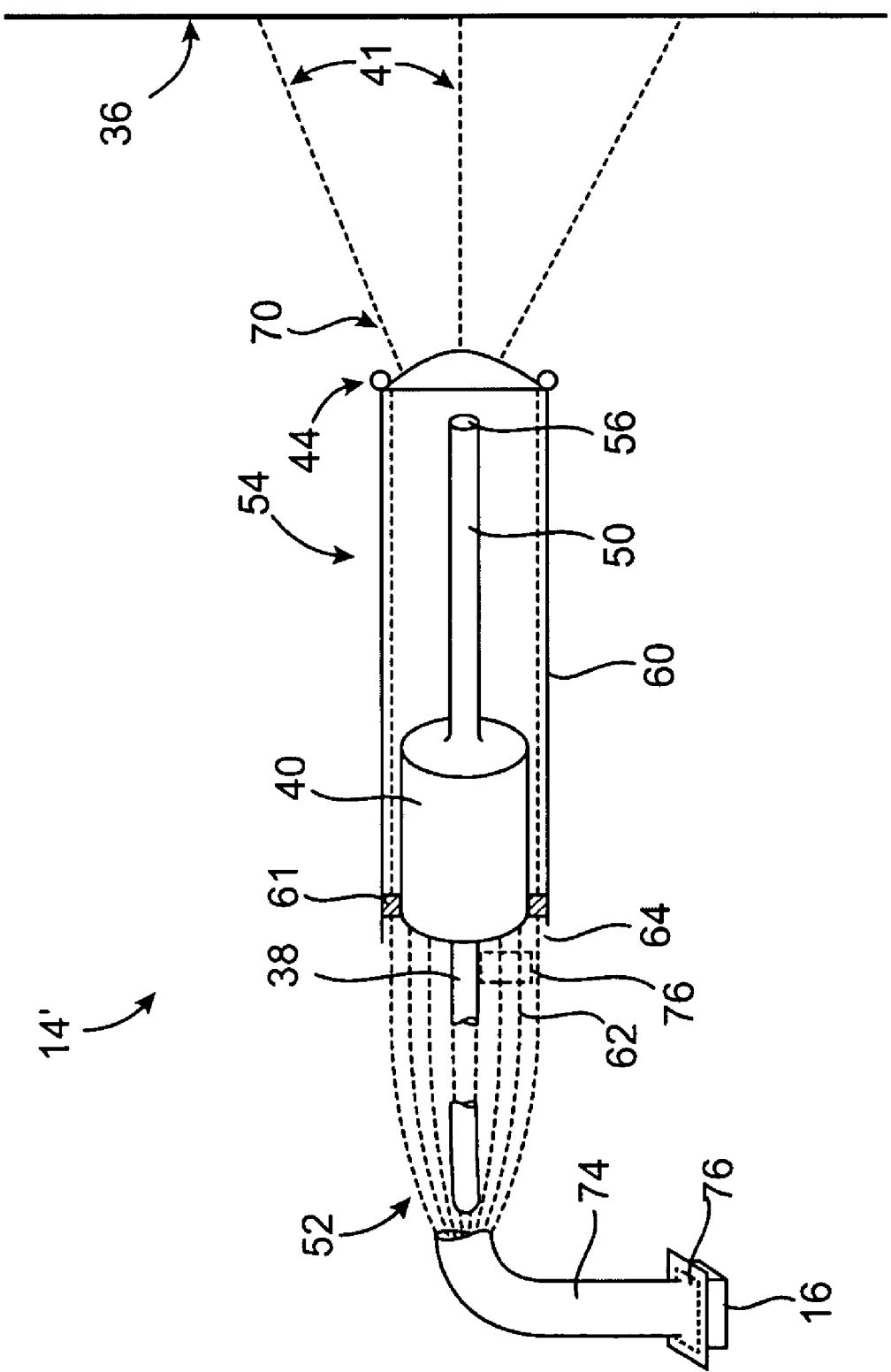
FIG. 3 illustrates a simplified imaging catheter that incorporates the scanning fiber of the present invention.

As shown in FIGS. 2 and 3, in a preferred embodiment, the scanning element 34 is in the form of a cantilevered optical fiber. The optical fibers 50 of the present invention may have any desired dimensions and cross-sectional shape. The optical fiber 50 may have a symmetrical cross sectional profile or an asymmetrical cross-sectional profile, depending on the desired characteristics of the device. An optical fiber 50 with a round cross-section will have substantially the same resonance characteristics about any two orthogonal axes, while an optical fiber with an asymmetric cross section (e.g., ellipse) will have different resonant frequencies about the major and minor axes. Additionally or alternatively, the optical fiber 50 may be tapered. The taper may be linear or non-linear. As can be appreciated, the type of taper will achieve different scanning parameters about the axes of the optical fiber.

Optical fiber 50 comprises a proximal portion 52 and a distal portion 54 that comprises a distal tip 56. Light from the light source 26 will enter into waveguide 38, which in most embodiments is the proximal portion 52 of the optical fiber, and out of the distal tip 56. Optical fiber 50 is typically fixed along at least one point of the optical fiber so as to be cantilevered. The distal portion 54 is free to be deflected so as to serve as the scanning element. To achieve the deflection of the distal portion 54 of the optical fiber, the optical fiber 50 will be coupled to drive assembly 40. In one preferred embodiment, the drive assembly is a piezoelectric assembly that is able to deflect the optical fiber in two dimensions. While preferred drive assemblies are piezoelectric assemblies, in alternative embodiments, the drive assembly 40 may comprise a permanent magnet, a electromagnet, an electrostatic drive, a sonic drive, an electro-mechanical drive, or the like.

A drive signal from controller 20 delivers power to the drive assembly 40. The current and voltage of the drive signal causes the piezoelectric drive assembly to deflect the distal tip 56 of the optical fiber 50 in a desired scan pattern in at least one dimension (and preferably two dimensions). A variety of different scan patterns may be implemented by the drive signal. One preferred 2-D scan pattern encompassed by the present invention is a spiral scan pattern. The spiral scan pattern is created by synchronizing an amplitude modulated horizontal sinusoidal vibration drive signal and a vertical sinusoidal vibration drive signal. Typically, the horizontal and vertical drive signals are driven with a 90 degree phase shift between them. As can be appreciated, the spiral scan pattern is merely one example of a scan pattern and other scan patterns, such as a rotating propeller scan pattern, a raster scan pattern, a line pattern, and the like, may be used by the present invention to scan the illumination spot on the target area.

The distal portion 54 may be driven at a variety of different frequencies, but the deflection of the distal tip 56 of the optical fiber is typically carried out substantially at a mechanical or vibratory resonant frequency (or harmonics of the resonant frequency) of the cantilevered portion of the optical fiber 54. As can be appreciated if desired, optical fiber 50 may also be driven at a non-resonant frequency, but is typically within a Q-factor of the resonant frequency. As can be appreciated, the point of connection between optical fiber 50 and driving assembly 40 and other physical properties of optical fiber 50 will effect the frequency of the drive signal needed to drive the optical fiber 50 at or near resonance. Hence, any manufacturing variations, even for same model types, will typically cause a variation in characteristics of the device, such as the resonant frequency of the distal portion 54 of the optical fiber.

FIG. 3 illustrates a specific embodiment of a flexible fiber scanning endoscope/catheter 14' of the present invention. In the illustrated embodiment, fiber scanning endoscope/catheter device 14' comprises a flexible, substantially tubular body 60 that houses the components of the beam scanning device. Drive assembly 40 is in the form of a tubular piezoelectric piezoceramic drive assembly that is coupled around a portion of optical fiber 50 and is spaced from the body with one or more collars 61. Piezoelectric drive assembly 40 is typically configured to resonate the optical fiber in at least two dimensions. Drive assembly 40 is driven with a drive signal supplied from the drive electronics in the controller 20 through leads 62. In one configuration, drive assembly 40 comprises five leads-an +x lead, -x lead, +y lead, -y lead, and a ground lead.

A detection assembly 44 may comprise one or more detectors positioned in or on the housing 60. Detection assembly 44 comprises one or more detectors that are in communication with a detection circuitry of controller 20 or another part of the controller 20 through leads 64. The detectors may be disposed anywhere on or within body 60 and positioned adjacent the distal portion 54 of optical fiber 50 so as to capture backscattered light reflected off of the target area 36. In the illustrated embodiment, the detectors are positioned at the distal end of housing 60.

The detection assembly 44 may comprise a variety of different detector types that receive light reflected from the target area. For example, the detection assembly in body 60 may comprise a light detector (such as a photodetector) that produces electrical signal that are conveyed through leads 64 to the base station 12. Alternatively, the detection assembly 44 may comprise one or more collector fibers (not shown) that transmit light reflected from the target area to photodetectors in the base station 12.

The detectors may be stationary relative to the optical fiber 50 or the detectors may be part of the optical fiber 50. The detector response is synchronized to the drive signal through controller and is used to determine a brightness of the small portion of target area 36 that corresponds to the illumination spot 42 at the given point in time. Light reflected from the target area 36 may be collected by detection assembly 44 and the light itself (via the collector fiber) or electric signals (via the photodetector) that correspond to the collected light may transmitted back to the controller 20 and/or memory 24 (or image storage device 32) for processing.

Theoretically, only a single light detector is needed to capture the backscattered light to generate a monochrome or black and white image. To generate a full-color image, three light detectors may be used. Each of the light detectors may be configured to filter different colors (e.g., blue, green, or red light transmissions). Such detectors are referred to herein as RGB detectors. Silicon-based semiconductor photodiodes (such as Si-PIN type) are useful for visible and near IR light detection because of their high sensitivity, low cost, small size, high speed, and ruggedness. Photodiodes, such as InGaAs material photodiodes, are useful for embodiment of the present invention that use IR optical detection. Since the resolution of the integrated optical scanning technique does not depend on size and number of light detectors, if desired, light detectors may be disposed on most or all of the available space adjacent the distal end of the optical fiber 50 for the purpose of increasing and discriminating between signal levels.

As shown in FIG. 3, the scanning fiber devices 14 of the present invention may include one or more lenses 70 to focus the imaging light, to provide better resolution and an improved FOV. In one embodiment, one or more lenses are disposed at a distal end of the housing. The lenses may be fixedly coupled to the housing or the lenses may be movable within the housing relative to each other. In other embodiments, a lens 70 may be coupled to the distal end 56 of the optical fiber and move and change orientation with the distal end 56 of the optical fiber. Any combination of lenses may be used in the devices of the present invention to provide or adjust optical properties of the scanning fiber device. For example, lenses may be used to adjust the focal plane, to collimate light, change the FOV, change resolution, or the like.

As can be appreciated, different combinations of the lenses of the scanning beam device 14' may affect the field of view (FOV) that is achievable. However, the scanning beam devices 14 of the present invention can generally provide linear scan patterns with a FOV between about 1 degree and about 90 degrees at 5 kHz scan frequencies. For circular 2D scan pattern, the present invention may provide a FOV between about 1 degree and about 90 degrees. As can be appreciated, variations in the type of lenses 70, the position of the lenses 70, the dimensions of the optical fibers, drive/actuation assembly, and other operating parameters of the scanning fiber device will change the field of view and other characteristics of the device.

As shown in FIG. 3, the leads 62 from the piezoelectric driving assembly 40, the leads 64 from the detectors (or the proximal end of the collector fibers), and the waveguide 38 extend proximally from the distal cylindrical housing 60 into a flexible cable 74. The proximal ends of the leads 62, 64 and the waveguide 38 extend into the connector member 16 that is disposed at a proximal end of cable 74. When the connector member 16 is mated with the interface 18 on the base station, appropriate connections are made with the leads 62, 64 and waveguide 38 to create a power path, detector path, a data path, an illumination path, and other communication paths between the base station 12 and the scanning beam device 14', respectively.

While not shown in FIG. 2 or 3, the housing 60 of the scanning beam devices 14 of the present invention may optionally comprise a deflectable distal tip portion so as to improve the ability of the housing to be advanced through a body lumen to the target area. The mechanism for deflecting the distal tip portion of the housing 60 may comprise one or more wires or electrical means for actuating the distal tip. Such deflection mechanisms (or the leads of the deflection mechanism) may also extend through housing 60, flexible cable 74 and to the connector member 16.

The devices of the present invention have a plurality of different characteristics that will vary from device to device. The type of device used for the particular procedure will typically depend on the requirements of the imaging procedure. For example, for smaller body lumens, a smaller housing and cable will be needed. Hence a size, number, and type of detectors, lenses, housing, and maximum deflection will likely be different than the larger scanning beam devices. Differences in the capabilities and components of the different scanning beam devices 14 will require different control routines for generating the drive signals, constructing images, etc. for the specific device 14. If proper control routines are not used for the selected canning beam device 14, the base station will not be able to properly operate the scanning fiber device 14 and may not be able to use all the capabilities of the scanning fiber device.

To provide the capability to properly operate the base station 12 and scanning fiber device 14, a memory 76, such as a non-volatile memory, may be incorporated into each of the different scanning beam devices 14 of the present invention. The memory 76 may take on a variety of forms, but is typically a non-volatile memory. The non-volatile memory includes, but is not limited to a FLASH memory, EEPROM, non-volatile RAM, battery packed up RAM, magnetic data storage, EPROM, PROM, ROM, or the like.

The non-volatile memory 76 may be disposed anywhere on the scanning fiber device 14. For example, as shown in FIG. 3, the memory 76 may be incorporated into the connector member. Alternatively, the memory may be incorporated into a portion of housing 60 or into any portion of cable 74.

Upon connection of the connector member 16 with the interface 18, power from power source 22 energizes memory 76 so as to create a data path between the controller 20 and the non-volatile memory 76. As can be appreciated, the connection of the connector member 16 with interface 18 also creates other connections, as will be described below.

Depending on the configuration of base station 12, memory 76 may contain a variety of different data. For example, in the simplest embodiment, a unique identifier may be stored in memory 76. The unique identifier may reference a portion of data from a look up table in which the portion of the look up table contains the relevant parametric data of the scanning fiber device. Unique identifier may be any identifying element, but is typically a unique serial number of the device. Controller 20 may be programmed to read the unique identifier from memory 76 upon connection of the device 14 to the base station. First, the controller may compare the unique identifier from memory 76 to a database of identifiers to determine if the identifier is acceptable and compatible with the base station. If the unique identifier is found in the look-up table, controller 20 may thereafter be programmed to access and read parametric data from a look up table or a database to generate and configure the control routine for the device 14.

The database of unique identifiers (and the associated operating parameters associated with the unique identifiers) may be stored locally in memory 76 or memory 24, or it may be stored in a remote server. Base station 12 may have a network connection (not shown) so that controller 20 may access the database over a network, such as a local area network (LAN), a wide area network (WAN), or the Internet. Even if memory 24 contains the database of unique identifiers, the network connection may be used to update the database stored in memory 24. Advantageously, as new devices are manufactured, the manufacturer can update the database to include the new device identifier and related parametric data.

In addition to the unique identifier or as an alternative to the unique identifier, parametric data of the device may be contained in memory 76. Upon determining that the device is compatible, controller may generate or reconfigure the control routine using the parametric data on memory 76. Controller 20 may be programmed to download the parametric data from memory 76 upon connection of the device 14 to the base station, and temporarily (or permanently) store the parametric data in memory 24. The parametric data may be input into an algorithm and a control routine for the device 14 may be generated by controller 20.

Providing the parametric data on memory 76 or 24 has a number of advantages. First, by having all of the parametric data stored on the memory, manufacturing tolerances can be relaxed. Instead of requiring that all devices of a specific model match a specific characteristic (e.g., resonant frequency), the devices of the present invention may be manufactured using reduced tolerances. Instead of testing the manufactured device to determine whether or not the characteristics match a predetermined criteria (and potentially re-manufacturing the device until the device meets the criteria), the device can be tested to determine the resonant frequency, and the device-specific data may be stored on the memory 76. Thereafter, the controller may use the device-specific data to generate a control routine that substantially matches the resonant frequency of the device. Second, having memory 76 in device 14 reduces the setup time prior to performing each imaging procedure, as the particular parameters of the scanning fiber device may automatically be accessed by the controller 20 of base station 12. Instead of performing a time consuming, full calibration setup routine to determine the parameters and capabilities of the device, a shorter calibration routine may be performed, which will reduce the overall time of the procedure.

As another alternative, instead of containing parametric data, memory 76 may comprise the actual control routine (e.g., drive signals, scan pattern, etc.) for operating device 14. During manufacturing, the parametric data for the device may be entered into an algorithm to generate the control routine. Thereafter, the control routine may then be stored in memory 76 and the control routine will be accessed by controller 20 when attached to the base station 12. If desired, a plurality of control routines may be stored on memory 76. Each of the different control routine would correspond to specific situations, such as specific environmental conditions, etc.

While the type of parametric data in memory 76 will vary depending on the capabilities of the base station and the device, the following is a non-limiting list of parametric data that may be on the memory and used by controller to generate the control routine for the device: serial number, model type, date of manufacture, date of expiration, drive assembly characteristics (e.g., type of drive assembly, current limits, voltage limits, etc.), detection assembly characteristics (e.g., type of detectors, number of detectors, stereo capability, color capability, detector responses), optical fiber characteristics (e.g., material, diameter, length, parametric data for real time control), resonant frequency of the device, resonant frequency range for the device, housing characteristics (e.g., deflectable distal tip, diameter, length, flexibility, etc.), imaging characteristics (e.g., lens parameters, number of lenses, types of lenses, focus capability, zoom capability), image correction (e.g., distortion corrections, color corrections, etc.), resolution, display setup information, therapy capability, extra channels, bend parameters, and the like.

Some examples of how some of the above listed data will be utilized by controller will now be described. It should be appreciated that any combination of the data may be stored on memory 76, and any combination of the parametric data or control routines described herein are encompassed by the present invention.

In one configuration, the data on the memory 76 may be used to configure the operator controls in base station 12. The data my indicate the capabilities of the scanning beam device and may disable or enable various operator controls on the user interface 26.

In another configuration, the parametric data stored on memory 76 may include the resonant frequency for the optical fiber 50. Controller 50 will read the resonant frequency information and may reconfigure the drive signal and control routine to match the resonant frequency accordingly.

In other configurations, the parametric data stored on memory 76 may be used to establish a search range for determining the resonant frequency of the optical fiber 50. Because resonance frequency may change with the temperature, time from the date of manufacture, etc., it may be desirable to store on memory 76 a range of search, e.g., X kHz±Y kHz. Consequently, after connecting the device 14 to the base station 12, control module 20 will only calibrate the device within the frequencies X kHz±Y kHz to determine the resonant frequency of the device. Instead of searching the entire range of frequencies, the calibration will search a limited range. Consequently, the setup time and number of calibration steps are reduced.

Memory 76 may be used to track and limit the usage of device 14. Memory 76 is useful for both single-use devices and re-usable devices. In one configuration, memory 76 may include a date of manufacture and/or an expiration date. Controller 20 may read the date of manufacture and/or the expiration date, and if a predetermined amount of time has passed from the date of manufacture or if the expiration date has been exceeded, the controller may be prevented from using the device.

Additionally or alternatively, memory 76 may include use limits for the device. The use limits may include a maximum amount of time the device may be used for, a maximum number of times that the device may be coupled to the base station, a maximum number of procedures, or the like. In such embodiments, controller 20 may write to memory 76 during and/or after its use. For example, the device's usage history may be written to memory 76 to include the date of usage, the time of usage, the number of times the device has been coupled to a base station, or the like. For single-use devices, the controller may write data onto the memory 76 after it's first usage that would prevent subsequent usage of the single-use device. Upon re-coupling of the device 14 to the base station, the controller will compare the usage history on memory 76 to the use limits. If the usage history meets or exceeds the use limits, the controller will prevent subsequent procedures from being performed with the device 14.

In addition to writing usage data to memory 76, controller 20 may write additional data onto memory 76 during or after imaging of the target area. For example, the data written onto memory 76 may include, how long the device was used, a quality of performance of the device, a modified look-up table for image construction, or the like, a calculated resonant frequency for the device, or the like. The writing of data onto the memory 76 may thereafter be used for later procedures with the device. Alternatively, the data written onto the memory 76 may be used to improve the efficiency of use of the device in its later use. For example, if a quality of performance of the device is poor, the controller may be prevented from using the device again until the device is tested and recalibrated in calibration chamber 33.

Figure 4:
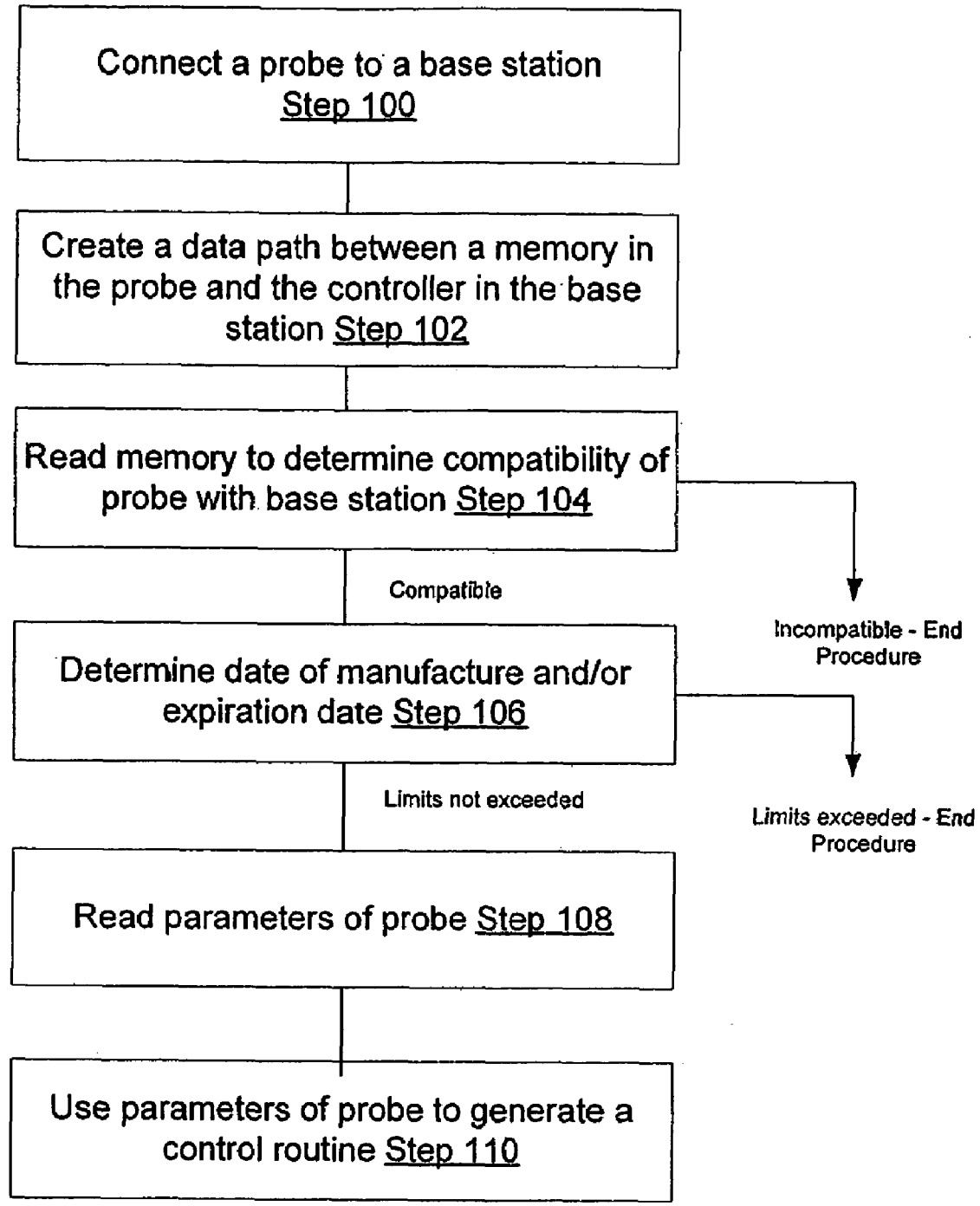
FIG. 4 schematically illustrates a method of the present invention.

FIG. 4 illustrates one example of a configuration routine that may be performed by the systems 10 of the present invention. As can be appreciated, the illustrated routine is merely an example, and other configuration routines with fewer or more steps may be implemented.

In the setup procedures of the present invention, the device 14 may be placed in a calibration chamber 33 in the base station 12 to be calibrated. At step 100, the user activates a power switch to base station 12 and connects connector member 16 to interface 18 of base station 12. At step 102, power is delivered from the base station 12 to the connector member 16 to create a data path between memory 76 and controller 20 of the base station. At step 104, controller 20 will read the memory 76 to identify the device and to determine if attached device is compatible to the base station. Determination of whether device is compatible with the base station may be carried out using any method known in the art. Typically, compatibility of the SFD and the base station is determined through a unique device identifier, such as a serial number or model number. The unique identifier may be downloaded to controller and compared with a look up table or database of all identifiers that are compatible with that particular base station 12. Preventing unknown or non-approved scanning fiber devices from being connected to the base station will provide safety measures to the patient.

If it is determined that device 14 is incompatible with the base station, controller 20 will generate and display an error message on display 30 or otherwise indicate incompatibility of the device (e.g., audible beep) and the configuration routine ends. If it is determined that device is compatible with the base station, controller will continue the configuration routine and read additional data from memory 76 or 24. As can be appreciated, if memory 76 only has a unique identifier, controller will read the additional data (e.g., parametric data from a look up table) from memory 24 that is associated with the unique identifier of the device 14. In embodiments in which the memory 76 contains both the unique identifier and the parametric data, controller 20 will read the additional data (e.g., parametric data) from memory 76.

At step 106, controller may determine the date of manufacture of the device and/or an expiration date and compare the dates to the actual date. If a predetermined amount of time past the date of manufacture has been exceeded or if the date of the configuration routine is past the expiration date, the controller will generate and display an error signal that indicates that the device has expired or has exceeded its use limits.

At step 108, controller 20 reads the device parameters from memory 76. Parameters that are typically included on memory 76 (or look up table in memory 24) are the resonant frequency of the device or a resonant frequency "range" of the device. If a resonant frequency range is provided, controller 20 will send drive signals to drive assembly 40 within the resonant frequency range and the photosensitive position sensor 31 will track the illumination spot emitted from the device 14 and based on the signal from sensor 44 the controller may automatically select the frequency that it determines is the resonant frequency of the device.

Controller 20 may also determine the characteristics of the drive assembly 40, such as maximum voltage limits, the zoom capabilities, FOV associated with different voltages, focus capabilities of the device, and the like.

Characteristics of the optical fiber and housing 60 may also be stored in memory. The characteristics may provide any combination of cross-sectional dimensions, length, flexibility, material, deflectability of the distal portion of the housing, or the like. Such information may be used to change the display of information, light control, or the like.

The characteristics of the detection assembly may also be provided in memory. The detection assembly characteristics may provide information regarding the color capability of the detectors, the number of detectors, the stereo capability of the detectors, the position of the detectors, or the like.

Memory may optionally include image reconstruction look-up tables or algorithms. The tables or algorithms may be used to remap an image displayed or acquired by the device 14 of the present invention. Alternatively, the tables or algorithms may be used to remap the drive signal used to scan the optical fiber. A more complete description of the look-up tables and algorithms is in commonly owned, co-pending U.S. patent application Ser. No. 10/956,241, filed on Oct. 1, 2004, entitled "Remapping Methods to Reduce Distortions in Images," the complete disclosure of which is incorporated herein by reference.

In step 110, the parametric data will be used to generate or reconfigure the control routine that is used to operate the device 14 and base station 12 during the scanning procedure. After controller has processed the parametric data from the memory and generated a customized control routine for the device, the controller generates a message to the operator that indicates that the configuration routine has completed and that the device is ready for use. Thereafter, the device may be removed from the calibration chamber 33 and positioned adjacent the target area. For use in a minimally invasive medical procedure, the device may be advanced through a body lumen to the target area using conventional methods. The pixels of the image may optionally be temporarily stored in memory and the image reconstruction algorithms are applied to generate an image of the target area and to correct color and image distortions. Thereafter, the images are sent to the display and may optionally be captured permanently in memory.

Advantageously, the data on the memory 76 in the scanning beam device 14 reduces a setup time of the device and will allow the base station 12 to properly operate the attached scanning fiber device 14 while still providing the ability to operate a variety of other scanning beam devices, no matter what the resonant frequency of the scanning fiber device, the diameter of the scanning fiber, etc. Moreover, because the memory 76 will allow the base station to properly operate any compatible device 14, manufacturing tolerances may be relaxed and the manufacturing process may be less complex, and the overall costs of manufacture may be reduced. Consequently, the overall cost associated with manufacturing and using a scanning beam device is reduced drastically.

It is understood that the examples and embodiments described herein are for illustrative purposes only and that various modifications or changes in light thereof will be suggested to persons skilled in the art and are to be included within the spirit and purview of this application and scope of the appended claims. For example, in other embodiments, the devices of the present invention may have additional elements such as a spectrophotometer, a spectrum analyzer, thermal detectors, or the like. Numerous different combinations are possible, and such combinations are considered to be part of the present invention.

What is claimed is:

1. A method of operating a scanning beam device, the method comprising:
   providing a scanning beam device that comprises a memory in communication with a connector member;
   coupling the connector member to interface of a base station so as to create a data path between the memory and a controller of the base station;
   reading data from the memory of the scanning fiber device;
   generating a control routine for operating the scanning beam device based at least in part on the data read from the memory; and
   operating the scanning beam device with the control routine.

2. The method of claim 1 wherein reading data comprises determining if the scanning beam device is compatible with the base station.

3. The method of claim 1 wherein reading data comprises reading a unique identifier from the memory, wherein generating the control routine is based on parametric data associated with the unique identifier.

4. The method of claim 1 wherein the scanning beam device is a scanning fiber device, wherein reading data comprises reading resonant frequency data of the scanning fiber device from the memory,
   wherein operating the scanning fiber device comprises scanning an optical fiber of the scanning fiber device substantially at the resonant frequency.

5. The method of claim 1 wherein the scanning beam device is a scanning fiber device that comprises an optical fiber,
   wherein reading data comprises reading a resonant frequency range of the fiber from the memory, wherein generating the control routine comprises scanning through the resonant frequency range to determine the resonant frequency of the fiber,
   wherein operating the scanning fiber device comprises scanning the fiber substantially at the resonant frequency.

6. The method of claim 1 wherein reading data comprises reading a maximum drive voltage for a drive assembly of the scanned beam device from the memory,
   wherein operating the scanned beam device comprises driving the drive assembly at or below the maximum drive voltage during the control routine.

7. The method of claim 1 wherein reading data comprises reading an expiration data or date of manufacture from the memory, wherein operating the scanning beam device is prevented if the expiration date has past or if a predetermined amount of time has past from the date of manufacture.

8. The method of claim 1 wherein reading data comprises reading a zoom or focus capability of the scanning beam device from the memory,
wherein operating the scanning beam device comprises allowing zooming and focusing according to the zoom or focus capability data.

9. The method of claim 1 further comprising writing data to the memory.

10. The method of claim 9 wherein writing data comprises writing at least one of a performance data, history usage, date of usage, or duration of usage.

11. The method of claim 1 wherein the scanning beam device comprises a scanning fiber endoscope, a scanning fiber microscope, or a scanning fiber display.

12. The scanning beam device of claim 1 wherein the memory comprises a non-volatile memory.

13. A scanning beam device comprising:
a scanning element;
a drive assembly coupled to the scanning element to control scanning of a target;
a memory; and
a connector member in communication with the memory, the connector member configured for releasably coupling the scanning beam device to an interface in a base station, wherein coupling of the connector member to the interface in the base station creates a data path from the memory to a controller of the base station,
wherein operation of the scanning beam device is carried out with a control routine that is based at least in part on data transmitted from the memory to the controller.

14. The scanning beam device of claim 11 wherein the scanning element comprises a single optical fiber.

15. A scanning fiber device comprising:
a fiber comprising a proximal end and a distal end;
a drive assembly coupled to the fiber to control scanning of the distal end of the fiber;
a memory; and
a connector member in communication with the memory, the connector member configured for releasably coupling the scanning fiber device to an interface in a base station, wherein coupling of the connector member to the interface in the base station creates a data path from the memory to a controller of the base station,
wherein operation of the scanning fiber device is carried out with a control routine that is based at least in part on data transmitted from the memory to the controller.

16. The scanning fiber device of claim 15 wherein the data provides compatibility data so that upon transmission of acceptable compatibility data to the controller, the controller of the base station is allowed to drive the drive assembly.

17. The scanning fiber device of claim 15 wherein the data provides identification data, the identification data comprising a unique serial number or a model number.

18. The scanning fiber device of claim 17 wherein the identification data is referenced in a look up table stored in a database, wherein the controller accesses the look up table in the database to determine parameters of the scanning fiber device.

19. The scanning fiber device of claim 15 wherein the data provides a resonant frequency data for the fiber, wherein the control routine drives the drive assembly to the fiber at a frequency that substantially corresponds to the resonant frequency data.

20. The scanning fiber device of claim 15 wherein the data provides a resonant frequency range for the fiber, wherein the controller is configured to search the resonant frequency range to determine the resonant frequency of the fiber.

21. The scanning fiber device of claim 15 wherein the data provides fiber parametric data comprising at least one of fiber diameter, fiber bending and position control data, parametric data for real time control.

22. The scanning fiber device of claim 15 wherein the data provides drive assembly parametric data comprising at least one of maximum drive assembly voltage and drive assembly requirements.

23. The scanning fiber device of claim 15 wherein the data provides data regarding date of manufacture or an expiration date data of the scanned fiber device.

24. The scanning fiber device of claim 15 wherein the data provides zoom capability data of the scanning fiber device.

25. The scanning fiber device of claim 15 wherein the data provides detector parametric data comprising at least one of color capability or detector responses.

26. The scanning fiber device of claim 15 wherein the memory comprises a non-volatile memory.

27. The scanning fiber device of claim 15 wherein the memory is disposed within the connector member, wherein the base station provides power through the connector member and memory to create the data path between the controller of the base station and the memory.

28. The scanning fiber device of claim 15 wherein the drive assembly comprises at least one piezoelectric element.

29. The scanning fiber device of claim 15 wherein the connector member provides electrical and optical coupling to the base station.

30. The scanning fiber device of claim 15 wherein the scanning beam device is a scanning fiber endoscope, a scanning fiber microscope, or a scanning fiber display.

31. The scanning fiber device of claim 15 wherein the controller is configured to write data to the memory, wherein the data comprises at least one of a performance data, history usage, date of usage, or duration of usage.

32. A base station configured to operate a plurality of different scanning fiber devices, the base station comprising:
a housing comprising an interface that is configured to releasably receive a connector member of a scanning fiber device, the scanning fiber device comprising a memory in communication with the connector member,
a controller that is configured to be electrically coupled to the scanning fiber device through the interface;
a memory coupled to the controller, the memory configured to store a plurality of code modules which when executed by the controller cause the controller to:
read data from the memory of the scanning fiber device; and
generate a control routine for a drive assembly of the scanning fiber device to scan the fiber scanning device at a desired scan frequency,
wherein the control routine is generated at least in part on the data read through the interface and from the memory of the scanning fiber.

33. The base station of claim 32 wherein the housing comprises a calibration chamber that includes a photosensitive position sensor, wherein the calibration chamber is configured to receive the scanning fiber device.

34. The base station of claim 32 wherein power is transmitted through the interface to the memory of the scanning fiber device, wherein the power transmitted through the connector member and memory of the scanning fiber device creates a data path between the controller of the base station and the memory of the scanning fiber device.

35. The base station of claim 32 further comprising an waveguide configured to transmit a light to the scanning fiber device through the interface.

36. The base station of claim 34 wherein the waveguide comprises at least one of a laser source, visible light source, UV source, a RGB source, or an IR source.

37. The base station of claim 32 wherein the data comprises compatibility data, wherein transmission of acceptable compatibility data to the controller allows for application of the control routine.

38. The base station of claim 32 wherein the data from the memory of the scanning fiber device provides a unique identification data and the memory of the base station comprises parametric data of the scanning fiber device associated with the unique identification data, wherein the control routine generated will be based on part on the parametric data.

39. The base station of claim 32 wherein the data comprises resonant frequency data for the fiber scanning device, wherein the control routine is configured to drive the drive assembly to scan the fiber at a frequency that substantially corresponds to the resonant frequency data.

40. The base station of claim 32 wherein the data comprises a resonant frequency range for the fiber scanning device, wherein the controller is configured to search the resonant frequency range to determine the resonant frequency of the fiber,
wherein the control routine is configured to drive the drive assembly to scan the fiber at a frequency that substantially corresponds to the resonant frequency data.

41. The base station of claim 32 wherein the data comprises drive assembly parametric data comprising at least one of maximum drive assembly voltage and drive assembly requirements.

42. The base station of claim 32 wherein the data comprises a device expiration date or date of manufacture of the scanning fiber device, wherein if the date of expiration has passed or if a predetermined time has passed from the date of manufacture, the controller is prevented from initiating the control routine.

43. The base station of claim 32 wherein the data comprises zoom and/or focus capability data of the scanning fiber device.

44. The base station of claim 32 wherein the data comprises fiber parametric data comprising at least one of fiber diameter, fiber bending and position control data, and parametric data for real time control.

45. The base station of claim 32 wherein the data comprises detector parametric data comprising at least one of color capability and detector response.

46. The base station of claim 32 wherein the controller is configured to write data to the memory, wherein the data comprises at least one of a performance data, history usage, date of usage, or duration of usage.

47. A scanning fiber system comprising:
a base station comprising a controller coupled to a light source and a memory;
at least one scanning fiber device, each scanning fiber device comprising:
a scanning fiber comprising a proximal end and a distal end;
a drive assembly coupled to the fiber to control scanning of the distal end of the scanning fiber;
a connector member for coupling the scanning fiber device to an interface in the base station; and
a memory in communication with the connector member,
wherein coupling of the connector member from one of the fiber scanning devices into the interface in the base station creates a data path from the memory of the scanning fiber device to a controller of the base station and an optical path between the light source to the scanning fiber, wherein the controller of the base station is configured to:
read data from the memory of the scanning fiber device; and
initiate a control routine to drive the drive assembly of the scanning fiber device so as to scan the fiber scanning device at a desired scan frequency, wherein the control routine is generated at least in part on the data read from the memory of the scanning fiber.

48. A scanning fiber device comprising:
a fiber comprising a proximal end and a distal end;
a drive assembly coupled to the fiber to control scanning of the distal end of the fiber;
memory means; and
connector means in communication with the memory means, the connector means configured for releasably coupling the scanning fiber device to an interface means in a base station, wherein coupling of the connector means to the interface in the base station creates a data path from the memory means to a controller of the base station,
wherein operation of the scanning fiber device is carried out with a control routine that is based at least in part on data transmitted from the memory means to the controller.

* * * * *